United States Patent [19]

Block et al.

[11] 4,377,537
[45] Mar. 22, 1983

[54] PREPARATION OF ALKANE PHOSPHONIC AND PHOSPHINIC ACID ARYL ESTERS

[75] Inventors: Hans-Dieter Block, Cologne; Hans-Günther Fröhlen, Leverkusen, both of Fed. Rep. of Germany

[73] Assignee: Bayer Aktiengesellschaft, Leverkusen, Fed. Rep. of Germany

[21] Appl. No.: 222,221

[22] Filed: Jan. 2, 1981

[30] Foreign Application Priority Data

Jan. 19, 1980 [DE] Fed. Rep. of Germany ....... 3001895

[51] Int. Cl.³ .................................................. C07F 9/32
[52] U.S. Cl. ..................................... 260/969; 260/961
[58] Field of Search ................................. 260/961, 969

[56] References Cited

U.S. PATENT DOCUMENTS 3,261,890 7/1966 Gordon et al. ..................... 260/961

Primary Examiner—Anton H. Sutto
Attorney, Agent, or Firm—Sprung, Horn, Kramer & Woods

[57] ABSTRACT

A process for the preparation of an alkane phosphonic acid diaryl ester or an alkane phosphinic acid aryl ester of the formula

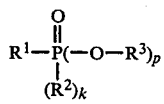

wherein
$R^1$ is $C_1$–$C_{20}$ alkyl or alkenyl group,
$R^2$ is a $C_1$–$C_{20}$ alkyl or alkenyl group or a $C_6$–$C_{10}$ aryl or aryloxy group,
$R^3$ is $C_6$–$C_{10}$ aryl group,
k is 0 or 1,
p is 1 or 2,
k+p=2,
plus an alkane phosphonic acid diaryl ester, alkane phosphinic acid aryl ester or phosphine oxide of the formula

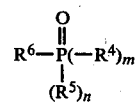

wherein
$R^4$ and $R^5$ each independently is $C_1$–$C_{20}$ alkyl group, a $C_6$–$C_{10}$ aryl group or a $C_6$–$C_{10}$ aryloxy group,
$R^6$ is $C_1$–$C_{20}$ alkyl or alkenyl group,
n and m each is 0, 1 or 2, and
n+m=2, comprising reacting an aryloxy compound of trivalent phosphorus of the formula

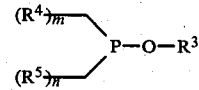

(a) with an alkyl phosphite or alkyl phosphonite of the formula

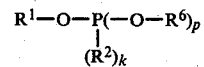

in the presence of an Arbusow catalyst, or (b) a rearrangement product formed in the presence of an Arbusow catalyst and of the formula

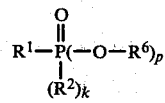

2 Claims, No Drawings

PREPARATION OF ALKANE PHOSPHONIC AND PHOSPHINIC ACID ARYL ESTERS

This invention relates to a process for the preparation of alkane phosphonic acid diaryl esters and alkane phosphinic acid aryl esters.

Alkane phosphonic acid diaryl esters and alkane phosphinic acid aryl esters are classes of compounds which have many possible applications. Alkane phosphonic acid diaryl esters used together with diols are suitable for the synthesis of high molecular weight polyphosphonates which are distinguished by their high fire resistance and heat resistance.

U.S. Pat. No. 3,578,731 describes the preparation of polyphosphonates having a low degree of polymerization by alkaline-catalysed ester interchange of phosphonic acid diaryl esters. U.S. Pat. No. 2,682,522 discloses a process for the preparation of polyphosphonates from phosphonic acid diaryl esters and aromatic dihydroxy compounds.

The numerous possibilities of practical application mentioned in the cited passages have created a demand for simple industrial syntheses of the alkane phosphonic acid diaryl esters required as starting materials.

Alkane phosphonic acid diaryl esters have hitherto been prepared by, for example, a reaction of alkane phosphonic acid dihalides with phenols in which hydrogen halide is liberated. Another known process is the Arbusow rearrangement of diaryl alkyl phosphites with alkylating agents such as alkyl iodides or sulphonic acid alkyl esters (see e.g. R. G. Laughlin, J. Org. Chem. 27, 3644 (1962)).

The known processes have not always been fully satisfactory since the alkane phosphonic acid dichlorides required for the first mentioned method are on the whole not commercially available substances nor are they generally available from commercial substances by a single stage reaction. The Arbusow rearrangement of diaryl alkyl phosphites is limited to special cases; short alkyl groups in particular cannot be rearranged to alkane phosphonic acid diaryl esters in known manner, e.g. with the aid of alkyl iodide as catalyst (see R. G. Laughlin, J. Org. Chem. 27, 3644 (1962)).

Two recent processes for the preparation of alkane phosphonic acid diaryl esters use the reaction of an alcohol, preferably methanol, with triaryl phosphites, e.g. triphenyl phosphite, in the presence of a rearrangement catalyst which is either a strong acid (German Application Le A 2747554) or methyl iodide, filed (M. L. Honig, E. D. Weil, J. Org. Chem. 42, 379 (1977)). In addition to the required alkane phosphonic acid diaryl ester, the displaced phenol is liberated in equimolar quantities. In both processes, the phenol liberated is heavily contaminated with phenol ethers. There has therefore been considerable interest in obtaining a process for the preparation of alkane phosphonic acid diaryl esters in which the disadvantages described are obviated.

The present invention solves this technical problem by producing alkane phosphonic acid diaryl esters and alkane phosphinic acid aryl esters in almost quantitative yields in a single stage reaction as the only products, preferably the only product, without the formation of some other unwanted product, from inexpensive, readily available starting materials produced on an industrial scale.

The present invention therefore provides a process for the preparation of alkane phosphonic acid diaryl esters and alkane phosphinic acid aryl esters corresponding to the general formula (Ia):

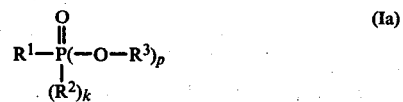

wherein
R$^1$ denotes a substituted or unsubstituted C$_1$–C$_{20}$ alkyl or alkenyl group,
R$^2$ denotes a substituted or unsubstituted C$_1$–C$_{20}$ alkyl or alkenyl group or a substituted or unsubstituted C$_6$–C$_{10}$ aryl or aryloxy group,
R$^3$ denotes a substituted or unsubstituted C$_6$–C$_{10}$ aryl group,
k denotes 0 or 1, and
P denotes 1 or 2, provided that k+P
together with alkane phosphonic acid diaryl esters, alkane phosphinic acid aryl esters or phosphine oxides corresponding to the general formula (Ib):

wherein
R$^4$ denotes a substituted or unsubstituted C$_1$–C$_{20}$ alkyl group, a C$_6$–C$_{10}$ aryl group or a C$_6$–C$_{10}$ aryloxy group,
R$^5$ stands for the same groups as R$^4$ independently of R$^4$,
R$^6$ stands for the same groups as R$^1$ independently of R$^1$, and
n and m stand for the integers 0, 1 and 2, with the proviso that n+m=2,
characterized in that aryloxy compounds of trivalent phosphorus, corresponding to the general formula (II):

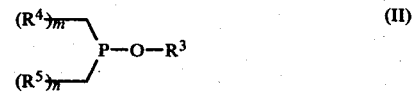

wherein R$^3$, R$^4$, R$^5$, n and m have the meaning indicated above and n+m=2, are reacted in the presence of Arbusow catalysts with alkyl phosphites or alkyl phosphonites corresponding to the general formula (IIIa):

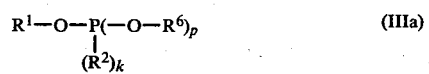

or rearrangement products thereof formed in the presence of Arbusow catalysts, corresponding to the general formula (IIIb):

wherein $R^1$, $R^2$, $R^6$, k and P have the meaning indicated above and $k+P=2$, the reaction being carried out using a molar ratio of (II):(III) of approximately P:1.

The process according to the invention may be represented in its general form by the following equation (1):

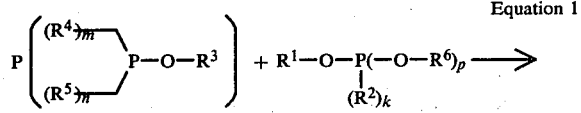

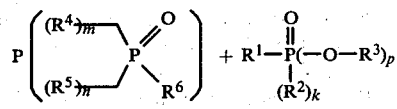

Without altering the other factors and compounds of this equation, the alkyl phosphite or alkyl phosphonite corresponding to the general formula (IIIa) may be replaced by the alkane phosphonate or alkane phosphinate of the general formula (IIIb), as shown in equation 2:

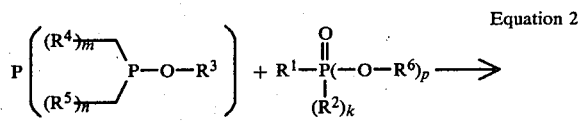

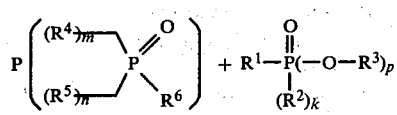

It is preferred, however, to employ that form of the process according to the invention in which the products corresponding to the general formulae (Ia) and (Ib) are identical, i.e. $R^1$ has the same meaning as $R^6$, $R^5=R^2$ or $O-R^3$, $R^4=O-R^3$, $n=k$ and $m=P$. In this preferred case, the reaction equation 1 assumes the simplified form of equation 3:

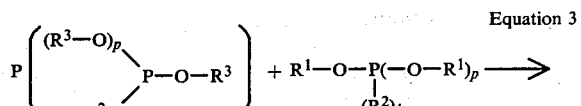

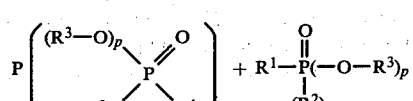

That embodiment of the process in which $k=0$ in Equation 3 is represented by Equation 4:

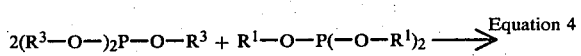

$$3R^1-\overset{O}{\underset{\|}{P}}(-O-R^3)_2$$

Equation 4 represents the reaction of a triaryl phosphite with a trialkyl phosphite to form a uniform alkane phosphonic acid diaryl ester.

That embodiment of the process according to the invention in which $k=1$ in Equation 3 is represented by Equation 5:

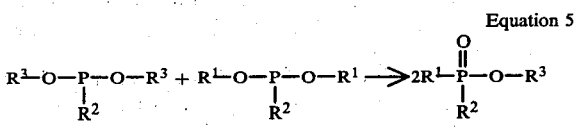

When $R^2$=an alkyl, alkenyl or aryl group, Equation 5 represents the reaction of a phosphonous acid diaryl ester with a phosphonous acid dialkyl ester to form a uniform alkane phosphinic acid aryl ester; when $R^2$=aryloxy, it represents the reaction of a triaryl phosphite with an aryl dialkyl phosphite to form a uniform alkane phosphonic acid diaryl ester.

If instead of using alkyl phosphites, their Arbusow rearrangement products, i.e. the alkane phosphonic acid dialkyl esters, are used as starting materials, Equation 4 is replaced by Equation 6:

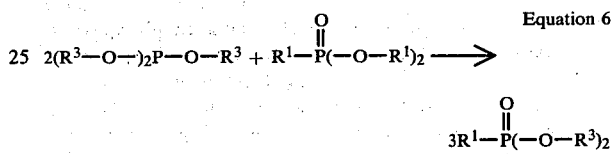

Equation 6 represents the reaction of a triaryl phosphite with a "symmetric" alkane phosphonic acid dialkyl ester to form a uniform alkane phosphonic acid diaryl ester.

If the phosphonous acid dialkyl esters or the aryl dialkyl phosphites in Equation 5 are replaced by their Arbusow rearrangement products, i.e. by the phosphinic acid alkyl esters or phosphonic acid alkyl aryl esters, Equation 7 is obtained:

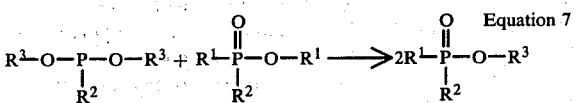

When $R^2$ denotes an alkyl, alkenyl or aryl group, Equation 7 represents the reaction of a phosphonous acid diaryl ester with a phosphonic acid alkyl ester to form a uniform alkane phosphinic acid aryl ester or, when $R^2$ denotes aryloxy, it represents the reaction of a triaryl phosphite with a phosphonic acid alkyl aryl ester to form a uniform alkane phosphonic acid diaryl ester.

Another preferred form of the process according to the invention represented by Equation 2 is that in which the aryloxy compound of trivalent phosphorus is one in which $R^4=R^5=O-R^3$ and the compound with which it is reacted is a compound having the structure corresponding to (IIIb) wherein $R^2=O-R^6$ and $R^1$ is different from $R^6$. For this special case, Equation 2 simplifies to Equation 8:

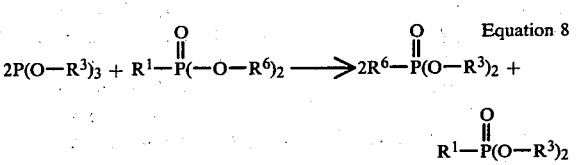

Some of the starting materials corresponding to the general formula (II) required for the process according to the invention that are the aryloxy compounds of trivalent phosphorus, i.e. phosphinous acid aryl esters, phosphonous acid diaryl esters and phosphorous acid triaryl esters, the latter two of which are preferred, are produced industrially in considerable quantities while many others can be prepared by known and simple processes (e.g. Houben Weyl, Methoden der Organo-Chemie, Stuttgart 1964, Volume XII, Part 2, pages 53–78, and Part 1, pages 208–211 and 324–331). The following are examples:

triphenyl phosphite
tris-p-cresyl phosphite
tris-m-cresyl phosphite
tris-p-chlorophenyl phosphite
tris-p-bromophenyl phosphite
tris-p-ethylphenyl phosphite
tris-p-isopropylphenyl phosphite
tris-m-isopropylphenyl phosphite
tris-o-isopropylphenyl phosphite
tris-p-tert.-butylphenyl phosphite
tris-p-methoxyphenyl phosphite
tris-(o,m,p)-cresyl phosphite
diphenyl cresyl phosphite
tris-(o,m,p)-isopropylphenyl phosphite
tris-octyl phenyl phosphite
tris-nonyl phenyl phosphite
diphenyl-$\beta$-naphthyl phosphite
diphenyl-p-phenyl-phenyl phosphite
o-phenylene-phenyl-phosphite
methane phosphonous acid-diphenyl ester
methane phosphonous acid-dicresyl ester
ethane phosphonous acid-diphenyl ester
vinyl phosphonous acid-diphenyl ester
cyclohexene phosphonous acid-diphenyl ester
chloromethane phosphonous acid diphenyl ester
butane phosphonous acid diphenyl ester
cyclohexane phosphonous acid diphenyl ester
benzene phosphonous acid diphenyl ester
p-dimethylaminobenzene phosphonous acid diphenyl ester
dimethyl phosphinous acid phenyl ester
dibutyl phosphinous acid phenyl ester
diphenyl phosphinous acid phenyl ester Some of the starting materials corresponding to the general formula (IIIa) which are required for the process of the invention, i.e. the alkyl phosphites and alkyl phosphonites, are also products produced on a large industrial scale while many others can be produced by known and simple processes (see e.g. Houben Weyl, Methoden der Organ. Chemie, 4th Edition, Stuttgart 1964, Volume XII, Part 1, pages 324–331, and Part 2, pages 53–78).

The following are examples:
trimethyl phosphite
triethyl phosphite
tris-i-propyl phosphite
tris-n-propyl phosphite
tris-i-butyl phosphite
tris-n-butyl phosphite
tris-n-hexyl phosphite
tris-2-ethyl hexyl phosphite
tri-dodecyl phosphite
tris-2-ethoxyethyl phosphite
tris-2-phenoxyethyl phosphite
tris-2-chloroethyl phosphite
tris-2-chloropropyl phosphite
triallyl phosphite
tribenzyl phosphite
phenyldiethyl phosphite
cyclohexylidene-1,4-bis-dimethyl phosphite
phenylene-1,3-bis-diethyl phosphite
butylidene-1,4-bis-dimethyl phosphite
methane phosphonous acid dimethyl ester
ethane phosphonous acid dimethyl ester
vinyl phosphonous acid dimethyl ester
chloromethane phosphonous acid dimethyl ester
butane phosphonous acid dimethyl ester
cyclohexane phosphonous acid dimethyl ester
benzene phosphonous acid dimethyl ester The process according to the invention may also be applied to substances which contain the structure (IIIa) repeatedly in the molecule. Each structural unit (IIIa) then behaves like a single molecule.

The rearrangement products corresponding to the general formula (IIIb) which may be used instead of the alkyl phosphites and alkyl phosphonites corresponding to the general formula (IIIa) in the process according to the invention are also known in large numbers and are easily prepared and some are industrial products. They may, of course, have been obtained by methods other than the rearrangement of the alkyl phosphites and alkyl phosphonites corresponding to the general formula (IIIa). Processes for their preparation are described in detail in Houben Weyl, Methoden der Org. Chemie, 4th Edition, Stuttgart 1964, Volume XII, pages 423–523 (phosphonic acid dialkyl esters) and pages 247–262 (phosphinic acid alkyl esters). Phosphonic acid esters and phosphinic acid esters corresponding to the general formula (IIIb) will be resorted to particularly when the group $R^1$ has such a structure that, for reasons inherent in the mechanism of the Arbusow rearrangement, it is not possible to carry out an Arbusow rearrangement from the alkyl phosphites and alkyl phosphonites corresponding to the general formula (IIIa) into the phosphonic acid dialkyl esters and phosphinic acid alkyl esters corresponding to the general formula (IIIb).

The following are examples of suitable phosphonic acid alkyl esters and phosphinic acid alkyl esters corresponding to the general formula (IIIb):
ethane phosphonic acid diethyl ester
methane phosphonic acid dimethyl ester
n-propane phosphonic acid di-n-propyl ester
butane phosphonic acid dibutyl ester
pentane phosphonic acid dipentyl ester
octane phosphonic acid dioctyl ester
ethane phosphonic acid dimethyl ester
i-propane phosphonic acid dimethyl ester
i-butane phosphonic acid dimethyl ester
cyclohexane phosphonic acid dimethyl ester
dodecane phosphonic acid dimethyl ester
2-methoxyethane phosphonic acid dimethyl ester
2-phenoxyethane phosphonic acid dimethyl ester
2-chloroethane phosphonic acid dimethyl ester
vinyl phosphonic acid dimethyl ester
allyl phosphonic acid dimethyl ester
benzene phosphonic acid dimethyl ester
2-cyanoethane phosphonic acid dimethyl ester
diphenyl phosphinic acid methyl ester
dimethyl phosphinic acid methyl ester The Arbusow catalysts required for carrying out the process according to the invention are either alkylating agents or very strong acids. Examples of alkylating agents which act as Arbusow catalysts include alkyl chlorides, alkyl bromides and alkyl iodides (the latter are preferred) in which the alkyl groups may carry numerous substituents (examples may be found in Houben Weyl, Methoden der Org. Chemie. 4th Edition, Stuttgart 1964, Volume XIII, Part 1, pages 433–446) and other known alkylating agents, such as sulphonic acid esters, sulphuric acid esters and sultones. Strong acids suitable as Arbusow catalysts include fluorosulphonic acids such as trifluoromethane sulphonic acid, perfluorobutane sulphonic acid and perfluorooctane sulphonic acid. If alkylating agents are used as Arbusow catalysts, it is advantageous to choose one which has the same alkyl group $R^6$ as the alkane phosphonic acid diaryl ester or alkane phosphinic acid aryl ester of the general formula (Ib) which is to be prepared. If, on the other hand, the alkylating agent used has an alkyl group different from the group $R^6$, some of the groups $R^6$ in the reaction product corresponding to the general formula (Ib) may be expected to be replaced by the alkyl group containing in the alkylating agent added. The Arbusow catalysts are used in quantities of about 0.01 to 10 mol %, based on the alkane phosphonic acid diaryl ester or alkane phosphinic acid aryl ester of the general formulae (Ib/Ib) which is to be prepared, preferably in quantities of about 0.5 to 5 mol %.

Although the aryloxy compound of trivalent phosphorus corresponding to the general formula (II) and the alkyl phosphite or alkyl phosphonite corresponding to the general formula (IIIa) or the alkane phosphonic acid alkyl ester or alkane phosphinic acid alkyl ester corresponding to the general formula (IIIb) react with each other in the molar ratios indicated in Equation 1 or Equation 2, the reactants for carrying out the reaction may also be used in different proportions. If pure end products are to be obtained in that case, however, those reactants which have been used in excess must be removed from the desired end product by the usual methods, e.g. distillation.

Instead of using the pure components (II) and (IIIa) or (IIIb), mixtures of these reactants may be used. In particular, reactants corresponding to the general formula (IIIa) and the general formula (IIIb) in both of which $R^1$, $R^2$ and $R^6$ have the same meaning may be used side by side in the reaction according to the invention. In that case, a uniform product is obtained just as if only one of the two substances, (IIIa) or (IIIb), had been used. Another advantageous variation of the process for the preparation of various alkane phosphonic acid diaryl esters or alkane phosphinic acid aryl esters in any desired proportion is the simultaneous use of two or more substances having the structure (IIIa) and/or (IIIb) in which $R^2$ and $R^6$ are identical and k and p have the same values but the groups $R^1$ are different from each other.

The process according to the invention represented by Equation 1 may be carried out in the presence or absence of solvents. Both the reactants and the reaction products as well as inert high boiling liquids may be used as solvents.

The process represented by Equation 1 may be carried out within a temperature range of from about 170° C. to about 300° C. The range of from about 200° C. to about 250° C. is preferred. The temperature may be controlled in the usual manner, e.g. by external cooling or by vapor cooling.

The process according to the invention is usually carried out at normal pressure but it may be advantageous to maintain a higher than atmospheric pressure in order to counteract the volatility of the Arbusow catalyst or of one of the reactants, or it may be advantageous to produce a reduced pressure, e.g. in order to enable vapor cooling to be carried out at the desired temperature range.

Although air has only a very slight influence on the course of the reaction, it is advisable to keep it away from the reaction mixture in order to prevent the risk of ignition at the reaction temperature and of oxidation of the trivalent phosphorus compounds used.

The process according to the invention may be carried out either continuously or intermittently. The intermittent method may be carried out either by introducing the aryloxy compound of trivalent phosphorus corresponding to the general formula (II) into the reaction vessel, with or without the Arbusow catalyst, and then adding the alkyl phosphite or alkyl phosphonite corresponding to formula (IIIa) or the alkane phosphonate or alkane phosphinate of formula (IIIb) at the reaction temperature, with or without the Arbusow catalyst, or by first introducing the alkane phosphonate or alkane phosphinate corresponding to formula (IIIb) into the reaction vessel, with or without the Arbusow catalyst, and then adding the aryloxy compound of trivalent phosphorus at the reaction temperature, with or without the Arbusow catalyst.

The Arbusow catalyst may be added either separately or together with the second component to be introduced. Additional quantities of the components already present in the reaction vessel or of alkyl phosphite or alkyl phosphonite corresponding to formula (IIIa) may be added in the course of the reaction. Owing to the risk of a Michaelis-Arbusow rearrangement of the alkyl phosphites or alkyl phosphonites of formula (IIIa), which would be difficult to control, or the sudden setting in of an exothermic reaction according to equation 1, it is less advisable to begin by introducing the alkyl phosphites or alkyl phosphonites corresponding to the general formula (IIIa) into the reaction vessel, alone or in admixture with the aryloxy compounds of trivalent phosphorus corresponding to formula (II) and/or in admixture with Arbusow catalysts, or to introduce the Arbusow catalyst into these substances in the reaction vessel. In cases where this reaction proceeds slowly or only slightly exothermally, and when only small reaction batches are used, the last mentioned methods as well as the introduction of mixtures of aryloxy compounds of trivalent phosphorus (formula II) and alkane phosphonate or alkane phosphinate (formula IIIb) as the first reactants into the reaction vessel may nevertheless be carried out quite successfully. The process may also be carried out continuously by the usual known methods and using the usual reaction apparatus.

The reaction products are obtained in a high degree of purity. The proportion of main product in the reaction mixture after completion of the reaction is frequently above 98%. Further purification can be achieved by the usual methods, e.g. withdrawal of lower boiling impurities in a vacuum. Distillation of the products yields very pure alkane phosphonic acid diaryl esters and alkane phosphinic acid aryl esters having a degree of purity of up to 99.9% and more. In addition to the methods of distillation or instead of these, washing processes may be employed for further purification, e.g. removal of the impurities by washing with water and with aqueous solutions of oxidizing agents, acids, alkalies or buffers.

The invention will be described more fully in the following examples (percentages refer to percentages by weight unless otherwise indicated):

EXAMPLE 1

A mixture of 64 g of trimethyl phosphite (0.52 mol), 310 g of triphenyl phosphite (95.7% commercial quality) and 2 ml of methyl iodide is heated with stirring. An exothermic reaction sets in at approximately 100° C. Heating is continued when this reaction has died down. The reaction again becomes exothermic at 210° C. The reaction mixture is cooled with air to prevent the temperature rising above 230° C. Stirring is continued for 10 minutes at 230° C. after the exothermic reaction has died down. After removal of the readily volatile constituents in a vacuum, 362 g of a crude methane phosphonic acid diphenyl ester having a degree of purity of 97% are obtained.

345 g of methane phosphonic acid diphenyl ester which is 99.8% pure are obtained by fractional distillation at a pressure of 1 mm Hg.

EXAMPLE 2

62 g of methane phosphonic acid dimethyl ester (0.5 mol) are mixed with 310 g of triphenyl phosphite (95.7% commercial quality) and 2 ml of methyl iodide and heated to 220° C. The heat of reaction liberated is removed in a light air stream so that the reaction temperature does not exceed 240° C. The exothermic reaction lasts approximately 20 minutes, after which the mixture is stirred for a further 10 minutes at 240° C. When the volatile constituents have been drawn off in a vacuum, the residue weighs 364 g and contains 87% of pure methane phosphonic acid diphenyl ester.

EXAMPLE 3

A mixture of about 82% by weight of triphenyl phosphite, about 17% by weight of trimethyl phosphite and about 0.8% by weight of methyl iodide are pumped into the first reactor of a three-stage reaction cascade, using a laboratory feed pump. The temperature is maintained at 240° C. in all stages. This means that the first reaction stage must be slightly cooled after the starting phase. The average residence time of the reaction mixture amounts to a total of approximately 1.5 hours, i.e. about 30 minutes for each reaction stage.

If the reaction volume is 15 liters, a total of 60.5 kg of trimethyl phosphite (488 mol), 300 kg of triphenyl phosphite (content: 95.7%, remainder phenol) (926 mol) and 2 liters of methyl iodide undergoes reaction.

The crude product isolated contains 95.0% of methane phosphonic acid diphenyl ester. For further purification, this crude product is distilled batchwise through a 1 meter column filled with porcelain saddle bodies measuring 10 mm. This distillation is carried out under a vacuum of 1 mm Hg pressure at the head of the column, using a distillate reflux ratio within the range of from 1:1 to 1:3. Methyl iodide, which escapes at the beginning of distillation as the lowest boiling component, is condensed in a receiver, cooled with dry ice and is thereby recovered almost quantitatively.

After complete working up, 336.1 kg of methane phosphonic acid diphenyl ester are obtained with an average degree of purity of 99.2%. The yield of pure methane phosphonic acid diphenyl ester is therefore 96.8% of the theoretical yield.

The purities could be adjusted to values ranging from 99.0% to 99.8% by altering the reflux ratio of vacuum distillation in the individual batches.

Since a substantial proportion of the distillation work is used up for the separation of the phenol which has been carried in with the triphenyl phosphite, markedly better results and simpler working up are obtained with pure triphenyl phosphite.

EXAMPLE 4

Using a laboratory feed pump, a mixture consisting of 82% of commercial triphenyl phosphite, which is 95.7% pure, 17% of trimethyl phosphite and 0.8% of methyl iodide is pumped into the first reactor of a two-stage reaction cascade. The temperature is 240° C. in both stages; the first reaction stage must always be slightly cooled. The average residence time of the reaction mixture amounts to a total of approximately 1 hour. The crude product isolated contains about 95% of methane phosphonic acid diphenyl ester.

EXAMPLE 5

A mixture of 82% of triphenyl phosphite (commercial quality), 17% of methane phosphonic acid dimethyl ester and 0.8% of methyl iodide are delivered into the first reactor of a two-stage reaction cascade by means of a laboratory feed pump. The temperature is 220° C. in both stages; the first reaction stage must be lightly cooled. The average residence time of the reaction mixture amounts to a total of approximately 1 hour. The crude product obtained has a methane phosphonic acid diphenyl ester content of about 89.7%.

A degree of conversion of 82% is already achieved in the first reactor, so that the residence time may be further reduced.

EXAMPLES 6–12

The procedure of Example 2 is repeated with minor variations in Examples 6–8 and 12, and that of Example 1 in Examples 9–11.

The variations are indicated in the following table. All data relate to a reaction mixture containing 310 g of triphenyl phosphite of commercial quality (95.7% according to gas-chromatographic analysis), taken as 1.0 mol.

| Example Number | Amount of Methane phosphonate (MPN)/ trimethyl phosphite (TMPI) (mol/mol TP) put into the process | Reaction temperature (°C.) | CH3I (ml/mol TP) put into the process | Yield of pure product (g/mol TP) | Yield of crude product (g/mol TP) | Content in the crude product (%) |
|---|---|---|---|---|---|---|
| 6 | 0.51 (MPN) | 250 | 2 | | 372 | 88.8 |
| 7 | 0.51 (MPN) | 260 | 1 | | 368* | 88.0 |
| 8 | 0.47 (MPN) | 230 | 2 | | 366** | 90.4 |
| 9 | 0.50 (TMPI) | 210 | 2 | | 370* | 91.3 |
| 10 | 0.52 (TMPI) | 230 | 1 | | 371* | 90.6 |
| 11 | 0.48 (TMPI) | 230 | 2 | 326 | 366** | 91.4 |

-continued

| Example Number | Amount of Methane phosphonate (MPN)/ trimethyl phosphite (TMPI) (mol/mol TP) put into the process | Reaction temperature (°C.) | $CH_3I$ (ml/mol TP) put into the process | Yield of pure product (g/mol TP) | Yield of crude product (g/mol TP) | Content in the crude product (%) |
|---|---|---|---|---|---|---|
| 12 | 0.45 (MPN) 0.10 (TMPI) | 230 | 2 | | 371 | 87.9 |

*Reaction time including after-reaction: 60 min.
**Product is deeply colored

EXAMPLE 13

68 g of methane phosphonic acid dimethyl ester (0.55 mol) are heated to 240° C. with 310 g of triphenyl phosphite of commercial purity and 1 ml of perfluorobutane sulphonic acid and stirred at this temperature for 30 minutes. The reacted mixture is then fractionally distilled. Methane phosphonic acid diphenyl ester has a boiling point of 135° C. at 1 mm Hg. The main fraction amounts to 345 g (92.7% of the theoretical yield) and has a degree of purity of 99.8%.

EXAMPLE 14

68 g of trimethyl phosphite (0.55 mol) are slowly heated together with 310 g of triphenyl phosphite of commercial purity and 1 ml of perfluorobutane sulphonic acid. An exothermic reaction sets in at 120° C. Heating is then continued up to 240° C. and the reaction mixture is maintained at this temperature for 40 minutes. The methane phosphonic acid diphenyl ester content in the crude product according to gas-chromatographic analysis is 93.4%.

EXAMPLE 15

A mixture of 30 g of methane phosphonic acid dimethyl ester (0.24 mol), 150 g of triphenyl phosphite of commercial purity and 1 ml of p-toluene sulphonic acid methyl ester is slowly heated to 230+ C. As reflux slows down, the temperature is raised to 250° C. and maintained at this level for 80 minutes. The proportion of methane phosphonic acid diphenyl ester in the crude product is 74.3%. In addition, the crude product contains inter alia triphenyl phosphite and methane phosphonic acid dimethyl ester.

EXAMPLE 16

A mixture of 64 g of methane phosphonic acid dimethyl ester (0.516 mol), 352 g of tris-p-cresyl phosphite (1.00 mol) and 2 ml of methyl iodide is slowly heated to 245° C. and tempered at this temperature for 30 minutes. Vacuum distillation yields 376 g of methane phosphonic acid di-p-cresyl ester ($Bp_{1\ mm}$ 144° C.), 98.6% pure.

EXAMPLE 17

85 g of triethyl phosphite (0.512 mol), 310 g of triphenyl phosphite of commercial purity and 1.5 ml of ethyl iodide are heated with stirring and maintained at 270° C. for 30 minutes. The crude product is found by gas-chromatographic analysis to contain 92.0% of ethane phosphonic acid diphenyl ester. 330 g of this product having a boiling point of $Bp_{1\ mm}$ 155° C. are obtained as main fraction by distillation.

EXAMPLE 18

104 g of tri-n-propyl phosphite (0.50 mol), 310 g of triphenyl phosphite of commercial purity and 2 ml of methyl iodide are mixed and heated. The mixture begins to boil at 220° C. As reflux slows down, the temperature is raised to 270° C. and the reaction mixture is then maintained at this temperature for 45 minutes. At the end of this time, the mixture is found by gas-chromatographic analysis to contain 65.5% of n-propane phosphonic acid diphenyl ester and 4.2% of methane phosphonic acid diphenyl ester.

EXAMPLE 19

67.4 g of tris-2-chloroethyl phosphite (0.25 mol), 155 g of triphenyl phosphite and 1 ml of methyl iodide are slowly heated to 250°–260° C. The temperature of the reaction mixture falls in the course of half an hour to 245° C. due to reflux formation. At the end of this process, the crude reaction product is found by gas-chromatographic analysis to contain 41.7% of 2-chloroethane phosphonic acid diphenyl ester among the volatile constituents.

EXAMPLE 20

68 g of vinyl phosphonic acid dimethyl ester (0.50 mol), 310 g of triphenyl phosphite and 2 ml of methyl iodide are heated to 210° C. The exothermic reaction lasts approximately 15 minutes. The reaction mixture is then kept at 210°–220° C. for a further 10 minutes. Apart from impurities, the mixture contains 62% of methane phosphonic acid diphenyl ester and 20.8% of vinyl phosphonic acid diphenyl ester (gas-chromatographic analysis). The main fraction obtained by fractional distillation amounts to 302 g of a mixture of methane phosphonic acid diphenyl ester and vinyl phosphonic acid diphenyl ester in proportions of 74:24 which cannot be further separated under these conditions (surface ratio determined by gas-chromatographic analysis).

EXAMPLE 21

134 g of 1-methoxy-1-oxo-phospholine-3 (1.02 mol), 310 g of commercial triphenyl phosphite and 2 ml of methyl iodide are together heated to 190°–200° C.; an exothermic reaction is observed to take place. After 40 minutes at this temperature, the reaction mixture is distilled under vacuum through a distillation bridge. The fraction distilling over between 123° C. and 138° C. (at 1 mm Hg total pressure) weighs 368 g and consists of methane phosphonic acid diphenyl ester and 1-phenoxy-1-oxo-phospholine in proportions of 61:34 (gas-chromatographic analysis).

EXAMPLE 22

84 g of 2-methoxyethane phosphonic acid dimethyl ester (0.50 mol), 310 g of triphenyl phosphite of commercial purity and 2 ml of methyl iodide are heated to 210° C. and after the exothermic reaction has died down the mixture is tempered at 212° C. for 15 minutes. The reaction mixture contains methane phosphonic acid diphenyl ester and 2-methoxyethane phosphonic acid diphenyl ester in a molar ratio of 2:1 ($^1$H—NMR analysis).

It will be appreciated that the instant specification and examples are set forth by way of illustration and not limitation, and that various modifications and changes may be made without departing from the spirit and scope of the present invention.

What is claimed is:

1. A process for the preparation of a phosphonic acid diaryl ester of the formula

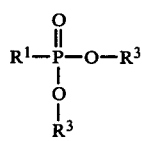

wherein
 $R^1$ is a $C_1$–$C_{20}$ alkyl or alkenyl group, and
 $R^3$ is a $C_6$–$C_{10}$ aryl group,
comprising reacting a triaryl phosphite of the formula

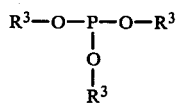

with approximately half the molar amount of an alkyl phosphite of the formula

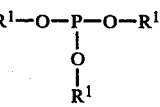

in the presence of an Arbusow catalyst at a temperature from about 170° to 300° C.

2. A process for the preparation of a phosphinic acid aryl ester of the formula

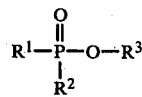

wherein
 $R^1$ is a $C_1$–$C_{20}$ alkyl or alkenyl group,
 $R^2$ is a $C_1$–$C_{20}$ alkyl or alkenyl group or an aryl group, and
 $R^3$ is a $C_6$–$C_{10}$ aryl group,
comprising reacting a phosphonous acid diaryl ester of the formula

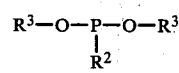

with approximately an equimolar amount of a phosphonous acid dialkyl ester of the formula

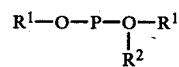

in the presence of an Arbusow catalyst at a temperature from about 170° to 300° C.

* * * * *